United States Patent [19]

Bailey et al.

[11] Patent Number: 5,489,708
[45] Date of Patent: Feb. 6, 1996

[54] SYNTHESIS OF IOVERSOL

[75] Inventors: Allan R. Bailey; Sharad S. Sathe, both of Manchester; Andre T. Spears, Florissant; Richard C. Wisneski, St. Louis; Mills T. Kneller, University City, all of Mo.

[73] Assignee: Mallinckrodt Medical, Inc., St. Louis, Mo.

[21] Appl. No.: 161,181

[22] Filed: Dec. 1, 1993

Related U.S. Application Data

[63] Continuation of Ser. No. 883,760, May 15, 1992, abandoned.

[51] Int. Cl.$^6$ .................................................. C07C 233/05
[52] U.S. Cl. .................................................. 564/153
[58] Field of Search .................................................. 564/153

[56] References Cited

U.S. PATENT DOCUMENTS

| | | | |
|---|---|---|---|
| 5,035,87 | 7/1991 | Sovak et al. | 424/5 |
| 5,004,835 | 4/1991 | Blaszkiewicz et al. | 564/153 |
| 5,019,371 | 5/1991 | Lin et al. | 424/5 |
| 5,043,152 | 8/1991 | Schaefer et al. | 424/5 |

FOREIGN PATENT DOCUMENTS 23365  11/1993  WIPO .

*Primary Examiner*—Glennon H. Hollrah
*Assistant Examiner*—Brian M. Burn
*Attorney, Agent, or Firm*—Brian K. Stierwalt

[57] ABSTRACT

The reduction of the O-alkyl isomer content of 5-[N-(2-acetoxyethyl)acetoxyacetamido] -N,N'-bis(2,3-diacetoxypropyl)-2,4,6-triiodoisophthalamide to thereby reduce and/or eliminate the production of impurities comparatively more difficult to remove during the purification of crude ioversol.

4 Claims, No Drawings

SYNTHESIS OF IOVERSOL

This is a continuation of application Ser. No. 07/883,760 filed on May 15, 1992, (now abandoned).

FIELD OF THE INVENTION

The present invention relates to the reduction of the O-alkyl isomer content of 5-[N-(2-acetoxyethyl)acetoxyacetamido] -N,N'-bis(2,3-diacetoxypropyl)-2,4,6-triiodoisophthalamide to thereby reduce and/or eliminate the production of those impurities comparatively more difficult to remove during the purification of ioversol.

BACKGROUND OF THE INVENTION

Ioversol is disclosed as a useful nonionic x-ray contrast agent in U.S. Pat. No. 4,396,598. 5-[N-(2 acetoxyethyl)-acetoxyacetamido]-N,N'-bis(2,3 -diacetoxypropyl)-2,4,6-triiodoisophthalamide, hereinafter referred to as "Compound A", having the following structure:

FORMULA I

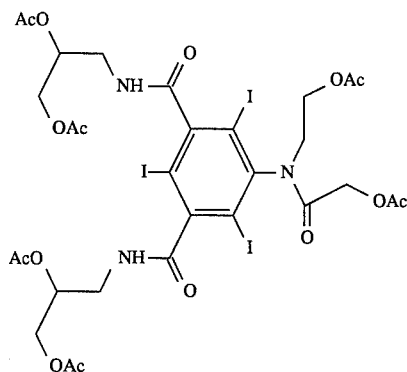

is an intermediate compound in the production of ioversol. The compound of Formula I and its use in the production of ioversol is likewise disclosed in U.S. Pat. No. 4,396,598 incorporated herein by reference. Compound A as disclosed in U.S. Pat. No. 4,396,598, may be produced by adding 2-bromoethylacetate and potassium carbonate to a solution of 5-acetoxyacetamido-N,N'-bis(2,3-diacetoxypropyl)- 2,4,6-triiodoisophthalamide, illustrated in Formula II below and hereinafter referred to as "Compound B",

FORMULA II

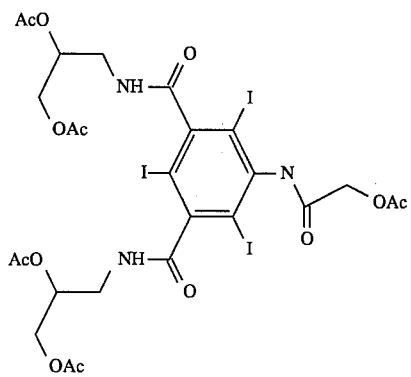

in dimethylsulfoxide and stirring until the reaction is complete. The resulting Compound A is then hydrolyzed with water containing sulfuric acid, preferably in small amounts within the range of approximately zero to 25 percent, to produce ioversol.

The procedure for producing ioversol is well documented and heretofore required an extensive purification process to remove impurities formed therein during the above-described synthesis.

An improved process that eliminates the need for such an extensive purification process for the purification of crude ioversol by significantly decreasing the impurities formed therein during synthesis, is desired as an enhanced and/or more cost efficient production method. It is an object of the present invention to meet these needs.

SUMMARY OF THE INVENTION

The acetoxyethyl isomer hereinafter referred to as the O-alkyl isomer of Compound A is an undesired impurity detectable during the synthesis of ioversol before the hydrolysis of the key intermediate, Compound A. Although the level of the O-alkyl isomer and its byproducts which result therefrom are reduced and/or eliminated through the current crude ioversol purification process, it is both costly and time consuming to do so.

The source of the O-alkyl isomer is from the O-alkylation reaction of Compound B using 2-bromoethylacetate as illustrated in Diagram 1 below.

DIAGRAM 1

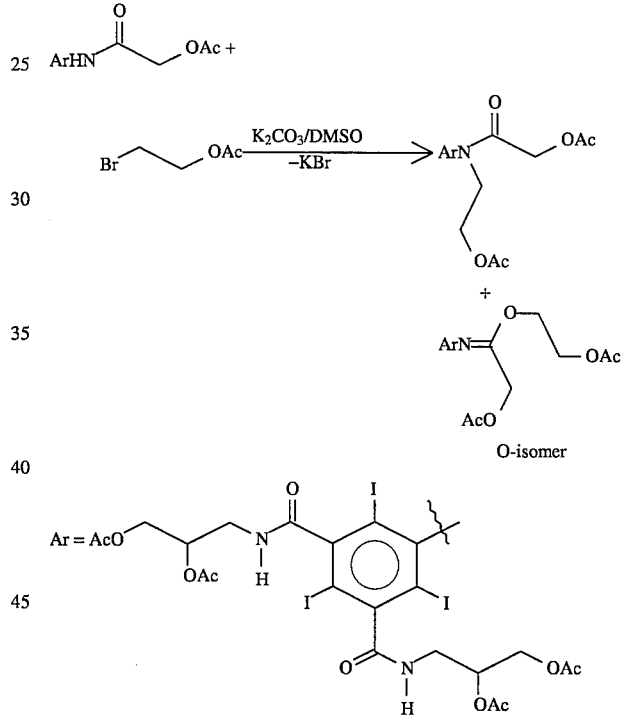

Since the O-alkyl isomer possesses an acetoxyacetimidate function, it may undergo either acid or base catalyzed hydrolysis to yield an amine, an ester, and/or alcoholic fragmentary products which are undesired, comparatively more difficult to remove impurities.

The O-alkyl isomer of Compound A is produced to the extent of approximately one to five percent under the conditions used to manufacture Compound A in the dimethylsulfoxide solvent. Use of other "polar aprotic" solvents, such as but not limited to, dimethylformamide, acetonitrile, dimethylacetamide, trichloroethane, carbon tetrachloride, dichloromethane, chloroform, dichloroethane, trichloroethylene and tetrachloroethylene, is also possible resulting in even higher levels of the O-alkyl isomer, i.e., approximately eight to thirty percent.

The present invention is an improved method of synthesizing ioversol which through a "selective hydrolysis" reaction most unwanted impurities are greatly reduced and/or eliminated. This provides the desired advantages in the later crude ioversol purification process by reducing the time and expense of purification which up until now was required.

DETAILED DESCRIPTION OF THE INVENTION

In order to greatly diminish and/or eliminate the production of various impurities known to form during the synthesis of ioversol or similar such nonionic contrast agents, the O-alkyl isomer of Compound A can be selectively hydrolyzed with water in a suitable solvent solution. Suitable solvent solutions include for example, but are not limited to, dimethylformamide, acetonitrile, dimethylacetamide, 1,1,1-trichloroethane, 1,1,2-trichloroethane, carbon tetrachloride, trichloromethane, dichloromethane, chloroform, dichloroethane, trichloroethylene and tetrachloroethylene wherein 1,1,2-trichloroethane (TCE) is preferable to achieve "selective hydrolysis". Selective hydrolysis describes a reaction whereby the O-alkyl isomer of Compound A is hydrolyzed while Compound A is comparatively unaffected. The achievement of such a selective hydrolysis reaction is both surprising and unexpected due to the structural similarities between Compound A and the O-alkyl isomer of Compound A. This selective hydrolysis reaction can be achieved by stirring the Compound A/solvent solution, containing water, at an elevated temperature within the range of 50 to 90 degrees Celcius. The O-alkyl isomer as a result of hydrolysis produces almost exclusively Compound B. When the unreacted Compound A, and the resulting small amounts of Compound B so produced, undergo acid hydrolysis to produce ioversol in the following synthetic step, Compound B is hydrolyzed to the ioversol impurity N,N'-bis(2,3-dihydroxypropyl)-5 -glycolamido-2,4,6-triiodoisophthalamide, hereinafter referred to as "Compound C". Compound C is later removed from the crude ioversol solution during the crude ioversol purification process with significantly greater ease and considerably less expense than that previously experienced in removing impurities formed from the O-alkyl isomer, such as polyols. Suitable purification processes for the present invention include, but are not limited to, one or more processes selected from the group consisting of crystallization, reverse osmosis, continuous deionization and liquid chromatography.

The present invention as just described is further illustrated by the following example, but is not intended to be limited thereby.

EXAMPLE 1

The Selective Hydrolysis of 2-acetoxyethyl-N-[3,5-bis((2,3 -acetoxypropylamino)carbonyl)-2,4,6-triiodophenyl]acetoxyacetimidate, i.e. O-alkyl isomer of Compound A One liter of a solution of Compound A in 1,1,2-trichloroethane, (TCE), containing a nominal level, i.e., approximately 3 percent, of the O-alkyl isomer, having a concentration of approximately 0.34 grams of Compound A per milliliter TCE was placed in a flask set up with stirring and distillation equipment. Under vacuum, 450 to 460 grams of TCE was distilled out of the solution at the pot temperature of about 50 to 55 degrees Celcius. The solution was then allowed to cool to a temperature of approximately 25 to 30 degrees Celcius under nitrogen atmosphere. 1.7 grams of deionized water was then added to achieve approximately a 0.5 percent weight/weight per Compound A. The solution was stirred and heated to 70 degrees Celcius under a nitrogen blanket and held at 70 degrees Celcius for two hours. The solution was then allowed to cool to 25 to 30 degrees Celcius and more TCE was distilled out under vacuum. The mixture was then heated to 80 degrees Celcius. Approximately 2,100 milliliters of amyl acetate was then added to the solution and Compound A was crystallized according to the standard process.

The typical HPLC results were as follows:

|  |  | O-alkyl Area % | Compound A Area % |
|---|---|---|---|
| Compound A in TCE | Run 1 | 2.995 | 94.130 |
| (starting material) | Run 2 | 3.310 | 94.450 |
| Dry Compound A | Run 1 | 0.179 | 81.391 |
| (after reaction) | Run 2 | 0.350 | 90.180 |

Along with the O-alkyl isomer, Compound A is also hydrolyzed to some extent as seen in the lower Compound A area percent purity. Partially hydrolyzed Compound A also produces ioversol. Thus the quality of ioversol remains unchanged. The reduction in the O-alkyl isomer level during the synthesis of ioversol leads to a significant reduction in the level of comparatively difficult to remove impurities formed. These impurities which form using the prior art process for synthesizing ioversol are considerably more difficult to remove during purification than those formed using the process of the present invention.

The improved method of synthesizing ioversol of the present invention is less expensive to purify, easier to perform and results in fewer comparatively more difficult to remove impurities.

Accordingly, having described our invention we claim:

1. A process for the production of ioversol from 5-[N-(2-acetoxyethyl)acetoxyacetamido] -N,N'-bis(2,3-diacetoxypropyl)- 2,4,6-triiodoisophthalamide and an O-alkyl isomer of 5-[N-( 2-acetoxyethyl) acetoxyacetamidol]-N,N'-bis(2,3-diacetoxypropyl)- 2,4,6-triiodoisophthalamide, comprising the steps of:

a.) selectively hydrolyzing said O-alkyl isomer of 5-[N-(2-acetoxyethyl) acetoxyacetamido]-N,N'-bis(2,3 -diacetoxypropyl)-2,4,6-triiodoisophthalamide n 5-[N-(2-acetoxyethyl)-acetoyacetamido] -N,N'-bis(2,3-diacetoyproyl)-2,4,6-triiodoisophthalamide with water in a suitable solvent under selectively hydrolyzing conditions to produce 5-acetoxyacetamido-N,N'-bis(2,3-diacetoxypropyl)2,4,6-triiodoisophthalamide in 5-[N-(2-acetoxyethyl) acetoxyacetamido]-N,N'-bis(2,3-diacetoxypropyl)-2,4,6-triiodoisophthalamide;

b.) acid hydrolyzing said 5-acetoxyacetamido-N,N'-bis(2,3-diacetoxypropyl)2,4,6-triiodoisophthalamide and 5-[N-(2-acetoxyethyl)acetoxyacetamido]-N,N-bis(2,3 -diacetoxypropyl)-2,4,6-triiodoisophthalamide under acid hydrolyzing conditions to produce ioversol and N,N'-bis-(2,3-dihydroxypropyl)-5-glycolamido-2,4,6-triiodoisophthalamide; and c.) purifying said ioversol produced to achieve purification thereof by removing said N,N'-bis-(2,3-dihydroxypropyl) 5-glycamido-2,4,6-triiodoisophthalamide therefrom.

2. The process of claim 1, wherein said selectively hydrolyzing conditions include achieving an elevated temperature within the range of 50 to 90 degrees Celcius.

3. The process of claim 1, wherein said purification is achieved through crystallization, reverse osmosis, continuous deionization, liquid chromatography or any suitable combination thereof.

4. The process of claim 1, wherein said solvent is selected from the group consisting of dimethylformamide, acetonitrile, dimethylacetamide, trichloromethane, carbon tetrachloride, dichloromethane, chloroform, dichloroethane, trichloroethylene, tetrachloroethylene, 1,1,1-trichloroethane and 1,1,2-trichloroethane.

* * * * *